United States Patent
Yamada et al.

(10) Patent No.: US 9,339,038 B2
(45) Date of Patent: May 17, 2016

(54) HERBICIDAL COMPOSITION

(71) Applicant: ISHIHARA SANGYO KAISHA, LTD., Osaka (JP)

(72) Inventors: Ryu Yamada, Shiga (JP); Hiroyuki Okamoto, Shiga (JP); Takashi Terada, Shiga (JP)

(73) Assignee: ISHIHARA SANGYO KAISHA, LTD., Osaka (JP)

( * ) Notice: Subject to any disclaimer, the term of this patent is extended or adjusted under 35 U.S.C. 154(b) by 0 days.

(21) Appl. No.: 14/382,620

(22) PCT Filed: Mar. 5, 2013

(86) PCT No.: PCT/JP2013/056032
§ 371 (c)(1),
(2) Date: Sep. 3, 2014

(87) PCT Pub. No.: WO2013/133287
PCT Pub. Date: Sep. 12, 2013

(65) Prior Publication Data
US 2015/0018214 A1 Jan. 15, 2015

(30) Foreign Application Priority Data

Mar. 9, 2012 (JP) ................................ 2012-052563

(51) Int. Cl.
*A01N 47/06* (2006.01)
*A01N 47/36* (2006.01)

(52) U.S. Cl.
CPC ............... *A01N 47/36* (2013.01); *A01N 47/06* (2013.01)

(58) Field of Classification Search
CPC ............................ A01N 47/06; A01N 47/36
See application file for complete search history.

(56) References Cited

U.S. PATENT DOCUMENTS

| | | | |
|---|---|---|---|
| 4,789,393 A * | 12/1988 | Hanagan | C07D 521/00 504/215 |
| 6,054,410 A | 4/2000 | Landes et al. | |
| 6,362,133 B1 | 3/2002 | Landes et al. | |
| 6,486,096 B1 | 11/2002 | Hacker et al. | |
| 6,750,177 B2 | 6/2004 | Hacker et al. | |
| 8,198,217 B2 | 6/2012 | Ohno et al. | |
| 2002/0198106 A1 | 12/2002 | Landes et al. | |
| 2003/0176284 A1 | 9/2003 | Hacker et al. | |
| 2010/0144526 A1 | 6/2010 | Ohno et al. | |
| 2014/0128263 A1 | 5/2014 | Yamada et al. | |
| 2015/0011391 A1 | 1/2015 | Yamada et al. | |

FOREIGN PATENT DOCUMENTS

| | | |
|---|---|---|
| CN | 1425297 | 6/2003 |
| DE | 19534910 | 3/1997 |
| JP | 2005-526736 | 9/2005 |
| JP | 2011-190197 | 9/2011 |
| WO | 00/08932 | 2/2000 |
| WO | 03/073853 | 9/2003 |
| WO | 2009/022598 | 2/2009 |
| WO | 2012/141277 | 10/2012 |
| WO | 2013/100178 | 7/2013 |

OTHER PUBLICATIONS

Machine translation of CN 1,425,297 (Jun. 2003).*
CABA abstract 1997:120810 (1997).*
Edenfield, M.W. et al., "Weed management in peanut (*Arachis hypogaea*) with pyridate and SAN 582 systems," Weed Technology, vol. 15(1), pp. 13-18 (2001).*
Extended European Search Report in respect to European Application No. 13758587.3, dated May 4, 2015.
"Green Kyllinga", Pest notes, XP055184059, Dec. 1, 2011, Retrieved from the Internet: URL: http://www.ipm.ucdavis.edu/PDF/PESTNOTES/pngreenkyllinga.pdf [retrieved on Apr. 17, 2015], pp. 1-4.
Littlefield et al., "The Effect of Nicosulfron Tank-Mixes and Time of Application on Sunrunner Peanut (*Arachis hypogaea*)", Weed Technology, vol. 9, No. 3, pp. 568-573, 1995.
Triebel, W., "Lido*Turbo*—Gegen alle Unkräuter mit einem Schlag", *Der Pflanzenarzt*, p. 23, 1999.
International Preliminary Report on Patentability for PCT/JP2013/056032 mailed Sep. 18, 2014, along with an English language translation.
International Search Report for PCT/JP2013/056032 mailed Apr. 16, 2013, along with an English language translation.

* cited by examiner

Primary Examiner — John Pak
(74) Attorney, Agent, or Firm — Greenblum & Bernstein, P.L.C.

(57) ABSTRACT

To provide a high active herbicidal composition having a broad herbicidal spectrum.
A herbicidal composition comprising synergistically effective amounts of (A) pyridate or its salt and (B) at least one sulfonylurea compound selected from the group consisting of flazasulfuron, nicosulfuron, trifloxysulfuron, chlorimuron and its alkyl ester, halosulfuron and its alkyl ester, and their salts.

13 Claims, No Drawings

HERBICIDAL COMPOSITION

TECHNICAL FIELD

The present invention relates to a herbicidal composition and a method for controlling undesired plants.

BACKGROUND ART

Patent Document 1 discloses a herbicidal composition comprising nicosulfuron and a specific known herbicide, and discloses pyridate as an example of the known herbicide.

However, it has not been known that a herbicidal composition comprising synergistically effective amounts of (A) pyridate or its salt and (B) at least one sulfonylurea compound selected from the group consisting of flazasulfuron, nicosulfuron, trifloxysulfuron, chlorimuron and its alkyl ester, halosulfuron and its alkyl ester, and their salts, has a synergistic herbicidal effect.

PRIOR ART DOCUMENT

Patent Document

Patent Document 1: Chinese Patent Publication No. 1425297

DISCLOSURE OF INVENTION

Technical Problem

At present, many herbicidal compositions have been developed and used, but there are a variety of types of undesired plants represented by weeds to be controlled. Further, undesired plants having lowered sensitivity to herbicides (herbicide-resistant weeds) emerged, and in some applications, practically, herbicides have only insufficient effects. The object of the present invention is to provide a high active herbicidal composition having a broader herbicidal spectrum, and a method for controlling undesired plants or inhibiting their growth using it. Another object of the present invention is to provide a method for controlling undesired plants having lowered sensitivity to herbicides.

Solution to Problem

It is possible to provide a high active herbicidal composition having a broad herbicidal spectrum by combination of (A) pyridate or its salt and (B) at least one sulfonylurea compound or its salt selected from the group consisting of flazasulfuron, nicosulfuron, trifloxysulfuron, chlorimuron and its alkyl ester, halosulfuron and its alkyl ester, and their salts.

That is, the present invention relates to a herbicidal composition comprising synergistically effective amounts of (A) pyridate or its salt (hereinafter referred to as compound A) and (B) at least one sulfonylurea compound selected from the group consisting of flazasulfuron, nicosulfuron, trifloxysulfuron, chlorimuron and its alkyl ester, halosulfuron and its alkyl ester, and their salts (hereinafter referred to as compound B). The present invention further relates to a method for controlling undesired plants or inhibiting their growth, which comprises applying the above herbicidal composition in synergistically effective amounts to the undesired plants or to a place where they grow. Still further, the present invention relates to a method for controlling green *kyllinga* or inhibiting its growth, which comprises applying a herbicidally effective amount of compound A to the green *kyllinga* or to a place where it grows.

Advantageous Effects of Invention

According to the present invention, it is possible to provide a high active synergistic herbicidal composition having a broad herbicidal spectrum The herbicidal composition of the present invention is capable of controlling a wide range of undesired plants emerging in agricultural fields or non-agricultural fields. It surprisingly represents a synergistic effect i.e. a herbicidal effect higher than the mere addition of the respective herbicidal effects of the active ingredients. Such a herbicidal composition of the present invention can be applied at a low dose as compared with a case where the respective active ingredients are applied individually. Thus, it is effective to reduce the environmental load on an area where the composition is applied or a surrounding area thereof.

When the herbicidal activity in a case where two active ingredients are combined, is larger than the simple sum of the respective herbicidal activities of the two active ingredients (the expected activity), it is called a synergistic effect. The activity expected by the combination of two active ingredients can be calculated as follows (Colby S. R., "Weed", vol. 15, p. 20-22, 1967).

$$E=(\alpha+\beta)-(\alpha\beta)/100$$

where $\alpha$: growth inhibition rate when treated with x (g/ha) of herbicide X, $\beta$: growth inhibition rate when treated with y (g/ha) of herbicide Y, E: growth inhibition rate expected when treated with x (g/ha) of herbicide X and y (g/ha) of herbicide Y.

That is, when the actual growth inhibition rate (measured value) is larger than the growth inhibition rate by the above calculation (calculated value), the activity by the combination can be regarded as showing a synergistic effect. The herbicidal composition of the present invention shows a synergistic effect when calculated by the above formula.

DESCRIPTION OF EMBODIMENTS

As for compound A, pyridate (common name) is O-6-chloro-3-phenylpyridazin-4-yl S-octylthiocarbonate.

As for compound B, flazasulfuron (common name) is 1-(4,6-dimethoxypyrimidin-2-yl)-3-(3-trifluoromethyl-2-pyridylsulfonyl)urea, nicosulfuron (common name) is 2-(4,6-dimethoxypyrimidin-2-ylcarbamoylsulfamoyl)-N,N-dimethylnicotinamide, trifloxysulfuron (common name) is 1-(4,6-dimethoxypyrimidin-2-yl)-3-[3-(2,2,2)-trifluoroethoxy)-2-pyridylsulfonyl]urea, chlorimuron (common name) is 2-(4-chloro-6-methoxypyrimidin-2-ylcarbamoylsulfamoyl)benzoic acid, and halosulfuron (common name) is 3-chloro-5-(4,6-dimethoxypyrimidin-2-ylcarbamoylsulfamoyl)-1-methylpyrazole-4-carboxylic acid.

The salt included in compound A or compound B may be any salt so long as it is agriculturally acceptable. Examples thereof include alkali metal salts such as a sodium salt and a potassium salt; alkaline earth metal salts such as a magnesium salt and a calcium salt; ammonium salts such as a monomethylammonium salt, a dimethylammonium salt and a triethylammonium salt; inorganic acid salts such as a hydrochloride, a perchlorate, a sulfate and a nitrate; and organic acid salts such as an acetate and a methanesulfonate.

The mixing ratio of compound A to compound B cannot generally be defined, since it varies depending upon various conditions such as the type of the formulation, the weather conditions, and the type and the growth stage of the undesired plants, and is preferably a mixing ratio to achieve the respective effective amounts (synergistically effective amounts) with which a synergistic effect is obtained when both are combined. It is, for example, from 500:1 to 1:2.5, preferably from 200:1 to 0.75:1 by the weight ratio.

In a case where compound B is flazasulfuron or its salt, the mixing ratio of compound A to compound B is, for example, from 500:1 to 1.3:1, preferably from 150:1 to 6:1 by the weight ratio.

In a case where compound B is nicosulfuron or its salt, the mixing ratio of compound A to compound B is, for example, from 500:1 to 2:1, preferably from 200:1 to 3:1, particularly preferably from 50:1 to 3:1 by the weight ratio.

In a case where compound B is trifloxysulfuron or its salt, the mixing ratio of compound A to compound B is, for example, from 500:1 to 2:1, preferably from 150:1 to 3:1 by the weight ratio.

In a case where compound B is chlorimuron or its alkyl ester, the mixing ratio of compound A to compound B is, for example, from 500:1 to 1.3:1, preferably from 60:1 to 3:1 by the weight ratio.

In a case where compound B is halosulfuron or its alkyl ester, the mixing ratio of compound A to compound B is, for example, from 50:1 to 1:2.5, preferably from 20:1 to 0.8:1 by the weight ratio.

The application amounts of compound A and compound B cannot generally be defined, since they should be properly adjusted depending upon the mixing ratio of compound A to compound B, the type of the formulation, the weather conditions, and the type and the growth stage of the undesired plants, and are preferably application amounts to be the respective effective amounts (synergistically effective amounts) with which a synergistic effect is obtained. The application amount of compound A is, for example, from 200 to 5,000 g/ha, preferably from 300 to 3,000 g/ha, and the application amount of compound B is from 10 to 500 g/ha, preferably from 15 to 400 g/ha.

In a case where compound B is flazasulfuron or its salt, the application amount of compound A is from 200 to 5,000 g/ha, preferably from 300 to 3,000 g/ha, and the application amount of compound B is from 10 to 150 g/ha, preferably from 20 to 50 g/ha.

In a case where compound B is nicosulfuron or its salt, the application amount of compound A is from 200 to 5,000 g/ha, preferably from 300 to 3,000 g/ha, and the application amount of compound B is from 10 to 100 g/ha, preferably from 15 to 100 g/ha.

In a case where compound B is trifloxysulfuron or its salt, the application amount of compound A is from 200 to 5,000 g/ha, preferably from 300 to 3,000 g/ha, and the application amount of compound B is from 10 to 100 g/ha, preferably from 20 to 100 g/ha.

In a case where compound B is chlorimuron or its alkyl ester, the application amount of compound A is from 200 to 5,000 g/ha, preferably from 300 to 3,000 g/ha, and the application amount of compound B is from 10 to 150 g/ha, preferably from 50 to 100 g/ha.

In a case where compound B is halosulfuron or its alkyl ester, the application amount of compound A is from 200 to 5,000 g/ha, preferably from 300 to 3,000 g/ha, and the application amount of compound B is from 100 to 500 g/ha, preferably from 150 to 400 g/ha.

The herbicidal composition of the present invention may be applied to undesired plants or may be applied to a place where they grow. Further, it may be applied at any time either before or after the emergence of the undesired plants. Further, the herbicidal composition of the present invention may take various application forms such as soil application, foliar application, irrigation application, and submerged application, and it can be applied to agricultural fields such as upland fields, orchards and paddy fields, and non-cropland such as ridges of fields, fallow fields, play grounds, golf courses, vacant lands, forests, factory sites, railway sides and roadsides.

The herbicidal composition of the present invention can control a wide range of undesired plants such as annual weeds and perennial weeds. The undesired plants to be controlled by the herbicidal composition of the present invention may, for example, be specifically cyperaceae such as green *kyllinga* (*Kyllinga brevifolia* Rottb. var. *leiolepis*), purple nutsedge (*Cyperus rotundus* L.), or amur *cyperus* (*Cyperus microiria* Steud.)); gramineae such as barnyardgrass (*Echinochloa crus-galli* L., *Echinochloa oryzicola* vasing.), summer grass (*Diqitaria ciliaris* (Retz.) Koeler), crabgrass (*Digitaria sanquinalis* (L.) Scop., *Diqitaria ischaemum* Muhl., *Digitaria adscendens* Henr., *Digitaria microbachne* Henr., or *Digitaria horizontalis* Willd.), green foxtail (*Setaria viridis* L.), goosegrass (*Eleusine indica* L.), johnsongrass (*Sorghum halepense* L.), annual bluegrass (*Poa annua* L.), panic grasses (*Panicum* spp.), guineagrass (*Panicum maximum* Jacq.), marmeladegrass, signal grass (*Brachiaria* spp.), surinam grass (*Brachiaria decumbens* Stapf.), paspalum (*Paspalum* spp.), *Imperata cylindrical* (L.) P. Beauv., *Miscanthus sinensis* Anderss., or *Andropogon virginicus* L.; scrophulariaceae such as persian speedwell (*Veronica persica* Poir.), corn speedwell (*Veronica arvensis* L.) or *Mazus miquelii* Makino.; compositae such as *Senecio vulgaris* L., *Sonchus oleraceus* L., *Gnaphalium spicatum* Lam., *Gnaphalium affine* D.Don, *Conyza sumatrensis* Walker, *Hypochoeris radicata* L., *Artemisia indica* var. maximowiczii, *Ixeris dentata* (Thunb.) Nakai., beggarticks (*Bidens* spp.), hairy fleabane (*Conyza bonariensis* (L.) Cronq.), horseweed (*Eriqeron canadensis* L.), dandelion (*Taraxacum officinale* Weber), or common cocklebur (*Xanthium strumarium* L.); leguminosae such as *Lespedeza striata* (Thunb.) Hook.et.Am., *Medicago lupulina* L., *Vicia sativa* subsp. Nigra, or white clover (*Trifolium repens* L.); caryophyllaceae such as sticky chickweed (*Cerastium glomeratum* Thuill.), or common chickweed (*Stellaria media* L.); euphorbiaceae such as *Euphorbia supina* Raf., garden spurge (*Euphorbia hirta* L.),or threeseeded copperleaf (*Acalypha australis* L); plantaqinaceae such as asiatic plantain (*Plantaqo asiatica* L.); oxalidaceae such as creeping woodsorrel (*Oxalis corniculata* L.); apiaceae such as lawn pennywort (*Hydrocotyle sibthorpioides* Lam.); violaceae such as violet (*Viola mandshurica* W. Becker); iridaceae such as blue-eyedgrass (*Sisyrinchium rosulatum* Bicknell); geraniaceae such as carolina geranium (*Geranium carolinianum* L.); labiatae such as purple deadnettle (*Lamium purpureum* L.) or henbit (*Lamium amplexicaule* L.); malvaceae such as velvetleaf (*Abutilon theophrasti* MEDIC.) or prickly sida (*Sida spinosa* L.); convolvulaceae such as tall morningglory (*Ipomoea purpurea* L.) or field bindweed (*Convolvulus arvensis* L.); chenopodiaceae such as common lambsquarters (*Chenopodium album* L.); portulacaceae such as common purslane (*Portulaca oleracea* L.); amaranthaceae such as redroot pigweed (*Amaranthus retroflexus* L.); solanaceae such as black nightshade (*Solanum nigrum* L.); polvqonaceeae such as spotted knotweed (*Polygonum lapathifolium*

L.), or green smartweed (*Polygonum scabrum* MOENCH); or cruciferae such as flexuous bittercress (*Cardamine flexuosa* WITH.).

The herbicidal composition of the present invention is very useful in practical application. For example, the herbicidal composition of the present invention has a remarkable synergistic effect, and has a favorable herbicidal activity even if the doses of the respective compounds A and B are small, and accordingly the impact on the surrounding environment can be suppressed. Further, the herbicidal composition of the present invention may reduce the phytotoxicity against useful crop plants as compared with a case where the respective compounds are applied individually. Further, a herbicidal composition having a long lasting herbicidal effect i.e. the long lasting residual activity, as compared with a case where compound A and compound B are applied individually, may be provided in some cases.

Further, the herbicidal composition of the present invention has such advantages that it has a high controlling effect against cyperaceae, has a high controlling effects against broadleaves, and inhibits growth of perennial gramineae.

In addition the herbicidal composition of the present invention has an excellent effect to control undesired plants having lowered sensitivity to herbicides (hereinafter sometimes referred to simply as weeds having lowered sensitivity) or to inhibit their growth. Such herbicides may, for example, be ALS (acetolactate synthase) inhibitors represented by sulfonylurea compounds. As an example of weeds having lowered sensitivity, green *kyllinga* may be mentioned. Further, the herbicidal composition of the present invention has an excellent effect in controlling, not only green *kyllinga* having lowered sensitivity but also other weeds having lowered sensitivity, or inhibiting their growth in some cases.

In the herbicidal composition of the present invention, a herbicidal compound other than compound A or compound B may be mixed if desired. Therefore, the range of weeds to be controlled, the time of application of the composition, the herbicidal activities, etc. may be improved to preferred directions.

Another herbicidal compound includes, for example, the following compounds (common names etc.). Even when not specifically mentioned here, in a case where such compounds have salts, alkyl esters, hydrates, different crystalline form, structural isomers etc., they are, of course, all included.

(1) Those which are believed to exhibit herbicidal effects by disturbing hormone activities of plants, such as a phenoxy type such as 2,4-D, 2,4-D-butotyl, 2,4-D-butyl, 2,4-D-dimethylammonium, 2,4-D-diolamine, 2,4-D-ethyl, 2,4-D-2-ethylhexyl, 2,4-D-isobutyl, 2,4-D-isoctyl, 2,4-D-isopropyl, 2,4-D-isopropylammonium, 2,4-D-sodium, 2,4-D-isopropanolammonium, 2,4-D-trolamine, 2,4-DB, 2,4-DB-butyl, 2,4-DB-dimethylammonium, 2,4-DB-isoctyl, 2,4-DB-potassium, 2,4-DB-sodium, dichlorprop, dichlorprop-butotyl, dichlorprop-dimethylammonium, dichlorprop-isoctyl, dichlorprop-potassium, dichlorprop-P, dichlorprop-P-dimethylammonium, dichlorprop-P-potassium, dichlorprop-P-sodium, MCPA, MCPA-butotyl, MCPA-dimethylammonium, MCPA-2-ethylhexyl, MCPA-potassium, MCPA-sodium, MCPA-thioethyl, MCPB, MCPB-ethyl, MCPB-sodium, mecoprop, mecoprop-butotyl, mecoprop-sodium, mecoprop-P, mecoprop-P-butotyl, mecoprop-P-dimethylammonium, mecoprop-P-2-ethylhexyl, mecoprop-P-potassium, naproanilide or clomeprop; an aromatic carboxylic acid type such as 2,3,6-TBA, dicamba, dicamba-butotyl, dicamba-diglycolamine, dicamba-dimethylammonium, dicamba-diolamine, dicamba-isopropylammonium, dicamba-potassium, dicamba-sodium, dichlobenil, picloram, picloram-dimethylammonium, picloram-isoctyl, picloram-potassium, picloram-triisopropanolammonium, picloram-triisopropylammonium, picloram-trolamine, triclopyr, triclopyr-butotyl, triclopyr-triethylammonium, clopyralid, clopyralid-olamine, clopyralid-potassium, clopyralid-triisopropanolammonium or aminopyralid; and others such as naptalam, naptalam-sodium, benazolin, benazolin-ethyl, quinclorac, quinmerac, diflufenzopyr, diflufenzopyr-sodium, fluroxypyr, fluroxypyr-2-butoxy-1-methylethyl, fluroxypyr-meptyl, chlorflurenol, chlorflurenol-methyl, aminocyclopyrachlor, aminocyclopyrachlor-methyl or aminocyclopyrachlor-potassium.

(2) Those which are believed to exhibit herbicidal effects by inhibiting photosynthesis of plants, such as a urea type such as chlorotoluron, diuron, fluometuron, linuron, isoproturon, metobenzuron, tebuthiuron, dimefuron, isouron, karbutilate, methabenzthiazuron, metoxuron, monolinuron, neburon, siduron, terbumeton, trietazine or metobromuron; a triazine type such as simazine, atrazine, atratone, simetryn, prometryn, dimethametryn, hexazinone, metribuzin, cyanazine, ametryn, cybutryne, triaziflam, indaziflam, terbutryn, propazine, metamitron or prometon; a uracil type such as bromacil, bromacyl-lithium, lenacil or terbacil; an anilide type such as propanil or cypromid; a carbamate type such as swep, desmedipham or phenmedipham; a hydroxybenzonitrile type such as bromoxynil, bromoxynil-octanoate, bromoxynil-heptanoate, ioxynil, ioxynil-octanoate, ioxynil-potassium or ioxynil-sodium; and others such as bentazone, bentazone-sodium, amicarbazone, methazole or pentanochlor.

(3) Quaternary ammonium salt type such as paraquat or diquat, which is believed to be converted to free radicals by itself to form active oxygen in the plant body and shows rapid herbicidal efficacy.

(4) Those which are believed to exhibit herbicidal effects by inhibiting chlorophyll biosynthesis of plants and abnormally accumulating a photosensitizing peroxide substance in the plant body, such as a diphenylether type such as nitrofen, chlomethoxyfen, bifenox, acifluorfen, acifluorfen-sodium, fomesafen, fomesafen-sodium, oxyfluorfen, lactofen, aclonifen, ethoxyfen-ethyl (HC-252), fluoroglycofen-ethyl or fluoroglycofen; a cyclic imide type such as chlorphthalim, flumioxazin, flumiclorac, flumiclorac-pentyl, cinidon-ethyl, fluthiacet or fluthiacet-methyl; and others such as oxadiargyl, oxadiazon, sulfentrazone, carfentrazone-ethyl, thidiazimin, pentoxazone, azafenidin, isopropazole, pyraflufen-ethyl, benzfendizone, butafenacil, saflufenacil, flupoxam, fluazolate, profluazol, pyraclonil, flufenpyr-ethyl, bencarbazone or ethyl [3-(2-chloro-4-fluoro-5-(3-methyl-2,6-dioxo-4-trifluoromethyl-3,6-dihydro-2H-pyrimidin-1-yl)phenoxy)pyridin-2-yloxy]acetate (SYN-523).

(5) Those which are believed to exhibit herbicidal effects characterized by bleaching activities by inhibiting chromogenesis of plants such as carotenoids, such as a pyridazinone type such as norflurazon, chloridazon or metflurazon; a pyrazole type such as pyrazolynate, pyrazoxyfen, benzofenap, topramezone or pyrasulfotole; and others such as amitrole, fluridone, flurtamone, diflufenican, methoxyphenone, clomazone, sulcotrione, mesotrione, tembotrione, tefuryltrione (AVH-301), bicyclopyrone, isoxaflutole, difenzoquat, difenzoquat-metilsulfate, isoxachlortole, benzobicyclon, picolinafen, beflubutamid, a compound disclosed in the claim of WO2003016286(SW-065, H-965), a compound disclosed in the claim of WO2009016841(KIH-3653, KUH-110), a compound disclosed in the claim of WO2005118530, a compound disclosed in the claim of WO2008065907, or a compound disclosed in the claim of WO2009142318.

(6) Those which exhibit strong herbicidal effects specifically to gramineous plants, such as an aryloxyphenoxypropionic acid type such as diclofop-methyl, diclofop, pyriphenop-sodium, fluazifop-butyl, fluazifop, fluazifop-P, fluazifop-P-butyl, haloxyfop-methyl, haloxyfop, haloxyfop-etotyl, haloxyfop-P, haloxyfop-P-methyl, quizalofop-ethyl, quizalofop-P, quizalofop-P-ethyl, quizalofop-P-tefuryl, cyhalofop-butyl, fenoxaprop-ethyl, fenoxaprop-P, fenoxaprop-P-ethyl, metamifop-propyl, metamifop, clodinafop-propargyl, clodinafop or propaquizafop; a cyclohexanedione type such as alloxydim-sodium, alloxydim, clethodim, sethoxydim, tralkoxydim, butroxydim, tepraloxydim, profoxydim or cycloxydim; and others such as flamprop-M-methyl, flamprop-M or flamprop-M-isopropyl.

(7) Those which are believed to exhibit herbicidal effects by inhibiting an amino acid biosynthesis of plants, such as a sulfonylurea type such as chlorimuron-ethyl, chlorimuron, sulfometuron-methyl, sulfometuron, primisulfuron-methyl, primisulfuron, bensulfuron-methyl, bensulfuron, chlorsulfuron, metsulfuron-methyl, metsulfuron, cinosulfuron, pyrazosulfuron-ethyl, pyrazosulfuron, azimsulfuron, flazasulfuron, rimsulfuron, nicosulfuron, imazosulfuron, cyclosulfamuron, prosulfuron, flupyrsulfuron-methyl-sodium, flupyrsulfuron, triflusulfuron-methyl, triflusulfuron, halosulfuron-methyl, halosulfuron, thifensulfuron-methyl, thifensulfuron, ethoxysulfuron, oxasulfuron, ethametsulfuron, ethametsulfuron-methyl, iodosulfuron, iodosulfuron-methyl-sodium, sulfosulfuron, triasulfuron, tribenuron-methyl, tribenuron, tritosulfuron, foramsulfuron, trifloxysulfuron, trifloxysulfuron-sodium, mesosulfuron-methyl, mesosulfuron, orthosulfamuron, flucetosulfuron, amidosulfuron, propyrisulfuron (TH-547), metazosulfuron, iofensulfuron or a compound disclosed in EP0645386; a triazolopyrimidinesulfonamide type such as flumetsulam, metosulam, diclosulam, cloransulam-methyl, florasulam, penoxsulam or pyroxsulam; an imidazolinone type such as imazapyr, imazapyr-isopropylammonium, imazethapyr, imazethapyr-ammonium, imazaquin, imazaquin-ammonium, imazamox, imazamox-ammonium, imazamethabenz, imazamethabenz-methyl or imazapic; a pyrimidinylsalicylic acid type such as pyrithiobac-sodium, bispyribac-sodium, pyriminobac-methyl, pyribenzoxim, pyriftalid or pyrimisulfan; a sulfonylaminocarbonyltriazolinone type such as flucarbazone, flucarbazone-sodium, propoxycarbazone-sodium, propoxycarbazone or thiencarbazone; and others such as glyphosate, glyphosate-sodium, glyphosate-potassium, glyphosate-ammonium, glyphosate-diammonium, glyphosate-isopropylammonium, glyphosate-trimesium, glyphosate-sesquisodium, glufosinate, glufosinate-ammonium, glufosinate-P, glufosinate-P-ammonium, glufosinate-P-sodium, bilanafos, bilanafos-sodium, cinmethylin or triafamone.

(8) Those which are believed to exhibit herbicidal effects by inhibiting cell mitoses of plants, such as a dinitroaniline type such as trifluralin, oryzalin, nitralin, pendimethalin, ethalfluralin, benfluralin, prodiamine, butralin or dinitramine; an amide type such as bensulide, napropamide, propyzamide or pronamide; an organic phosphorus type such as amiprofos-methyl, butamifos, anilofos or piperophos; a phenyl carbamate type such as propham, chlorpropham, barban or carbetamide; a cumylamine type such as daimuron, cumyluron, bromobutide or methyldymron; and others such as asulam, asulam-sodium, dithiopyr, thiazopyr, chlorthal-dimethyl, chlorthal or diphenamid.

(9) Those which are believed to exhibit herbicidal effects by inhibiting protein biosynthesis or lipid biosynthesis of plants, such as a chloroacetamide type such as alachlor, metazachlor, butachlor, pretilachlor, metolachlor, S-metolachlor, thenylchlor, pethoxamid, acetochlor, propachlor, dimethenamid, dimethenamid-P, propisochlor or dimethachlor; a thiocarbamate type such as molinate, dimepiperate, pyributicarb, EPTC, butylate, vernolate, pebulate, cycloate, prosulfocarb, esprocarb, thiobencarb, diallate, tri-allate or orbencarb; and others such as etobenzanid, mefenacet, flufenacet, tridiphane, cafenstrole, fentrazamide, oxaziclomefone, indanofan, benfuresate, pyroxasulfone, fenoxasulfone, dalapon, dalapon-sodium, TCA-sodium or trichloroacetic acid.

(10) MSMA, DSMA, CMA, endothall, endothall-dipotassium, endothall-sodium, endothall-mono(N,N-dimethylalkylammonium), ethofumesate, sodium chlorate, pelargonic acid, nonanoic acid, fosamine, fosamine-ammonium, pinoxaden, ipfencarbazone(HOK-201), aclolein, ammonium sulfamate, borax, chloroacetic acid, sodium chloroacete, cyanamide, methylarsonic acid, dimethylarsinic acid, sodium dimethylarsinate, dinoterb, dinoterb-ammonium, dinoterb-diolamine, dinoterb-acetate, DNOC, ferrous sulfate, flupropanate, flupropanate-sodium, isoxaben, mefluidide, mefluidide-diolamine, metam, metam-ammonium, metam-potassium, metam-sodium, methyl isothiocyanate, pentachlorophenol, sodium pentachlorophenoxide, pentachlorophenol laurate, quinoclamine, sulfuric acid, urea sulfate, methiozolin (MRC-01), etc.

(11) Those which are believed to exhibit herbicidal effects by being parasitic on plants, such as *Xanthomonas campestris, Epicoccosirus nematosorus, Epicoccosirus nematosperus, Exserohilum monoseras* or *Drechsrela monoceras*.

The herbicidal composition of the present invention may be prepared by mixing compound A and compound B, as active ingredients, with various agricultural additives in accordance with conventional formulation methods for agricultural chemicals, and applied in various formulations such as dusts, granules, water dispersible granules, wettable powders, tablets, pills, capsules (including a formulation packaged by a water soluble film), water-based suspensions, oil-based suspensions, microemulsions, suspoemulsions, water soluble powders, emulsifiable concentrates, soluble concentrates or pastes. It may be formed into any formulation which is commonly used in this field, so long as the object of the present invention is thereby met.

At the time of the formulation, compound A and compound B may be mixed together for the formulation, or they may be separately formulated.

The additives to be used for the formulation include, for example, a solid carrier such as kaolinite, sericite, diatomaceous earth, slaked lime, calcium carbonate, talc, white carbon, kaoline, bentonite, clay, sodium carbonate, sodium bicarbonate, mirabilite, zeolite or starch; a solvent such as water, toluene, xylene, solvent naphtha, dioxane, dimethylsulfoxide, N,N-dimethylformamide, dimethylacetamide, N-methyl-2-pyrrolidone or an alcohol; an anionic surfactant such as a salt of fatty acid, a benzoate, a polycarboxylate, a salt of alkylsulfuric acid ester, an alkyl sulfate, an alkylaryl sulfate, an alkyl diglycol ether sulfate, a salt of alcohol sulfuric acid ester, an alkyl sulfonate, an alkylaryl sulfonate, an aryl sulfonate, a lignin sulfonate, an alkyldiphenylether disulfonate, a polystyrene sulfonate, a salt of alkylphosphoric acid ester, an alkylaryl phosphate, a styrylaryl phosphate, a salt of polyoxyethylene alkyl ether sulfuric acid ester, a polyoxyethylene alkylaryl ether sulfate, a salt of polyoxyethylene alkylaryl ether sulfuric acid ester, a polyoxyethylene alkyl ether phosphate, a salt of polyoxyethylene alkylaryl phosphoric acid ester, a salt of polyoxyethylene aryl ether phosphoric acid ester, a naphthalene sulfonic acid condensed with formaldehyde or a salt of alkylnaphthalene sulfonic acid condensed with formaldehyde; a nonionic surfactant such as a sorbitan fatty acid ester, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, polyethylene glycol, a polyoxyethylene fatty acid ester, a polyoxyethylene sorbitan fatty acid ester, a polyoxyethylene glycerin fatty acid ester, a polyoxyethylene hydrogenated castor oil or a polyoxypropylene fatty acid ester; and a vegetable oil or mineral oil such as olive oil, kapok oil, castor oil, palm oil, camellia oil, coconut oil, sesame oil, corn oil, rice bran oil, peanut oil, cottonseed oil, soybean oil, rapeseed oil, linseed oil, tung oil or liquid paraffins. These additives may suitably be selected for use alone or in combination as a mixture of two or more of them, so long as the object of the present invention is met. Further, additives other than the above-mentioned may be suitably selected for use among those known in this field. For example, various additives commonly used, such as a filler, a thickener, an anti-settling agent, an anti-freezing agent, a dispersion stabilizer, a safener, an anti-mold agent, a bubble agent, a disintegrator and a binder, may be used. The mix ratio by weight% of the active ingredients to such various additives in the herbicidal composition of the present invention may be from about 0.001:99.999 to about 95:5, preferably from about 0.005:99.995 to about 90:10.

As a method of applying the herbicidal composition of the present invention, a proper method can be employed among various methods depending upon various conditions such as the application site, the type of the formulation, and the type and the growth stage of the undesired plants to be controlled, and for example, the following methods may be mentioned.

1. Compound A and compound B are mixed and formulated together, and the formulation is applied as it is.
2. Compound A and compound B are mixed and formulated together, and the formulation is diluted to a predetermined concentration with e.g. water, and as the case requires, a spreader (such as a surfactant, a vegetable oil or a mineral oil) is added for application.
3. Compound A and compound B are separately formulated, and the formulations are applied as they are.
4. Compound A and compound B are separately formulated, and as the case requires, the formulations are diluted to predetermined concentrations with e.g. water, and as the case requires, a spreader (such as a surfactant, a vegetable oil or a mineral oil) is added, and the formulations are applied.
5. Compound A and compound B are separately formulated, and the formulations are mixed when diluted to a predetermined concentration with e.g. water, and as the case requires, a spreader (such as a surfactant, a vegetable oil or a mineral oil) is added for application.

Preferred embodiments of the present invention will be described below, but the present invention is by no means restricted thereto.

(1) A herbicidal composition comprising synergistically effective amounts of (A) pyridate or its salt and (B) at least one sulfonylurea compound selected from the group consisting of flazasulfuron, nicosulfuron, trifloxysulfuron, chlorimuron and its alkyl ester, halosulfuron and its alkyl ester, and their salts.

(2) The composition according to the above (1), wherein (B) is at least one sulfonylurea compound selected from the group consisting of flazasulfuron, nicosulfuron, trifloxysulfuron and their salts.

(3) The composition according to the above (1), wherein (B) is chlorimuron, its alkyl ester or its salt.

(4) The composition according to the above (1), wherein (B) is halosulfuron, its alkyl ester or its salt.

(5) The composition according to the above (1), wherein (B) is at least one sulfonylurea compound selected from the group consisting of flazasulfuron, trifloxysulfuron, chlorimuron and its alkyl ester, halosulfuron and its alkyl ester, and their salts.

(6) The composition according to the above (1), wherein (B) is nicosulfuron or its salt.

(7) The composition according to the above (1), wherein herbicidally active ingredients are only (A) and (B).

(8) The composition according to the above (1), wherein herbicidally active ingredients are only pyridate and nicosulfuron.

(9) The composition according to the above (1), wherein (B) is flazasulfuron or its salt.

(10) The composition according to any one of the above (1) to (9), which contains (A) and (B) in amounts to achieve a herbicidal synergistic effect (herbicidally synergistically effective amount).

(11) The composition according to any one of the above (1) to (9), wherein the mixing ratio of (A) to (B) is from 500:1 to 1:2.5 by the weight ratio.

(12) A method for controlling undesired plants or inhibiting their growth, which comprises applying a herbicidally effective amount of a herbicidal composition comprising synergistically effective amounts of (A) pyridate or its salt and (B) at least one sulfonylurea compound selected from the group consisting of flazasulfuron, nicosulfuron, trifloxysulfuron, chlorimuron and its alkyl ester, halosulfuron and its alkyl ester, and their salts, to the undesired plants or to a place where they grow.

(13) A method for controlling undesired plants or inhibiting their growth, which comprises applying (A) pyridate or its salt and (B) at least one sulfonylurea compound selected from the group consisting of flazasulfuron, nicosulfuron, trifloxysulfuron, chlorimuron and its alkyl ester, halosulfuron and its alkyl ester, and their salts, in synergistically effective amounts to the undesired plants or to a place where they grow.

(14) The method according to the above (12) or (13), wherein the undesired plants are plants having lowered sensitivity to herbicides.

(15) The method according to the above (12) or (13), wherein the undesired plants are plants having lowered sensitivity to ALS inhibitors.

(16) The method according to the above (12) or (13), wherein the undesired plant is green *kyllinga*.

(17) The method according to the above (12) or (13), wherein the undesired plant is green *kyllinga* having lowered sensitivity to ALS inhibitors.

(18) The method according to the above (12) or (13), wherein (A) is applied in an amount to achieve a herbicidal synergistic effect (herbicidally synergistically effective amount) and (B) is applied in an amount to achieve a herbicidal synergistic effect (herbicidally synergistically effective amount).

(19) The method according to the above (12) or (13), wherein (A) is applied in an amount of from 200 to 5,000 g/ha, and (B) is applied in an amount of from 10 to 500 g/ha.

(20) A method for controlling green *kyllinga* or controlling its growth, which comprises applying a herbicidally effective amount of (A) pyridate or its salt to the green *kyllinga* or to a place where it grows.

(21) The method according to the above (20), wherein (A) is applied in an amount of from 200 to 5,000 g/ha.

(22) The method according to the above (20), wherein the green *kyllinga* is green *kyllinga* having lowered sensitivity to herbicides.

(23) The method according to the above (20), wherein the green *kyllinga* is green *kyllinga* having lowered sensitivity to ALS inhibitors.

(24) The method according to any one of the above (15), (17) and (23), wherein the ALS inhibitors are sulfonylurea compounds.

(25) The method according to the above (20), wherein a herbicidally effective amount of pyridate or its salt is applied to a place where manilagrass grows to control green *kyllinga* or inhibit its growth.

EXAMPLES

Now, the present invention will be described in further detail with reference to Examples. However, the present invention is by no means restricted to such specific Examples.

Test Example 1

Upland field soil was put into a 1/1,000,000 ha pot, and rhizomes of green *kyllinga* (*Kyllinga brevifolia* Rottb. var. *leiolepis*) were planted. On the 59th day after planting, to the green *kyllinga* in heading stage, predetermined amounts of EC formulation containing pyridate as an active ingredient (tradename: Pyridate 600EC, manufactured by BCP), WG formulation containing flazasulfuron as an active ingredient (tradename: SHIBAGEN DF, manufactured by Ishihara Sangyo Kaisha, Ltd.), WG formulation containing trifloxysulfuron Na salt as an active ingredient (tradename: Monument WG, manufactured by Syngenta Japan K.K.), SC formulation containing nicosulfuron as an active ingredient (tradename: ONEHOPE NYUZAI, manufactured by Ishihara Sangyo Kaisha, Ltd.), WG formulation containing halosulfuron-methyl as an active ingredient (tradename: INPOOL DF, manufactured by Nissan Chemical Industries, Ltd.) and WG formulation containing chlorimuron-ethyl as an active ingredient (tradename: ATTRACTIVE, manufactured by MARUWA Biochemical Co., Ltd.) were diluted with water in an amount corresponding to 2,000 L/ha, and applied for foliar treatment by a small sprayer.

On the 14th day after treatment, the state of growth of the green *kyllinga* was visually observed to determine the growth inhibition rate (%) in accordance with the following evaluation standard. The growth inhibition rate (%) (measured value) and the growth inhibition rate (%) (calculated value) calculated by the Colby's formula are shown in Table 1.

Growth inhibition rate (%)=0 (equivalent to the non-treated area) to 100 (complete kill)

TABLE 1

| Compound | Dose (g/ha) | Growth inhibition rate (%) of green *kyllinga* | |
|---|---|---|---|
| | | Measured value | Calculated value |
| Pyridate | 500 | 18 | — |
| | 2000 | 50 | — |
| Flazasulfuron | 50 | 33 | — |
| Trifloxysulfuron Na salt | 45 | 15 | — |
| Nicosulfuron | 80 | 15 | — |
| Halosulfuron-methyl | 375 | 10 | — |
| Chlorimuron-ethyl | 100 | 18 | — |
| Pyridate + Flazasulfuron | 2000 + 50 | 80 | 66 |

TABLE 1-continued

| Compound | Dose (g/ha) | Growth inhibition rate (%) of green *kyllinga* | |
|---|---|---|---|
| | | Measured value | Calculated value |
| Pyridate + Trifloxysulfuron Na salt | 2000 + 45 | 83 | 58 |
| Pyridate + Nicosulfuron | 500 + 80 | 43 | 30 |
| | 2000 + 80 | 78 | 58 |
| Pyridate + Halosulfuron-methyl | 500 + 375 | 35 | 26 |
| | 2000 + 375 | 73 | 55 |
| Pyridate + Chlorimuron-ethyl | 500 + 100 | 55 | 32 |
| | 2000 + 100 | 72 | 59 |

Test Example 2

Upland field soil was put into a 1/1,000,000 ha pot, and seeds of prickly sida (*Sida spinosa* L.) were sown. When the prickly sida reached 5.5 to 5.8-leaf stage, predetermined amounts of a wettable powder containing pyridate as an active ingredient (tradename: Lentagran WP, manufactured by BCP) and ONEHOPE NYUZAI (tradename) were diluted with water in an amount of corresponding to 1,000 L/ha and applied for foliar treatment by a small sprayer.

On the 14th day after treatment, the state of growth of the prickly sida was visually observed to determine the growth inhibition rate (%). The growth inhibition rate (%) (measured value) and the growth inhibition rate (%) calculated in the same manner as in the above Test Example 1 are shown in Table 2.

TABLE 2

| Compound | Dose (g/ha) | Growth inhibition rate (%) of prickly *sida* | |
|---|---|---|---|
| | | Measured value | Calculated value |
| Pyridate | 300 | 38 | — |
| Nicosulfuron | 15 | 30 | — |
| Pyridate + Nicosulfuron | 300 + 15 | 68 | 57 |

Test Example 3

Upland field soil was put into a 1/1,000,000 ha pot, and rhizomes of green *kyllinga* (*Kyllinga brevifolia* Rottb. var. *leiolepis*) were planted. When the green *kyllinga* reached 5-leaf stage, a predetermined amount of EC formulation containing pyridate as an active ingredient was diluted with water (in an amount corresponding to 2,000 L/ha) and applied for foliar treatment by a small sprayer.

On the 21st day after treatment, the state of growth of the green *kyllinga* was visually observed to determine the growth inhibition rate (%). The results are shown in Table 3.

TABLE 3

| Compound | Dose (g/ha) | Growth inhibition rate (%) of green *kyllinga* |
|---|---|---|
| Pyridate | 1200 | 90 |
| | 2400 | 100 |

Test Example 4

Upland field soil was put into a 1/1,000,000 ha pot, and rhizomes of green *kyllinga* (*Kyllinga brevifolia* Rottb. var. *leiolepis*) were planted. When the green *kyllinga* reached a height of from 5 to 7 cm, a predetermined amount of EC formulation containing pyridate as an active ingredient was diluted with water (in an amount corresponding to 2,000 L/ha) and applied for foliar treatment by a small sprayer. Further, on the 7th day after the foliar treatment, second treatment was carried out in the same manner on part of the green *kyllinga*.

On the 21st day after the first treatment, the state of growth of the green *kyllinga* was visually observed to determine the growth inhibition rate (%). The results are shown in Table 4.

TABLE 4

| Compound | Dose (g/ha) 1st treatment | Dose (g/ha) 2nd treatment | Growth inhibition rate (%) of green *kyllinga* |
|---|---|---|---|
| Pyridate | 2400 | — | 87 |
|  | 3600 | — | 89 |
|  | 1200 | 1200 | 100 |
|  | 2400 | 1200 | 100 |

Test Example 5

Upland field soil was put into a 1/300,000 ha pot, and rhizomes of green *kyllinga* (*Kyllinga brevifolia* Rottb. var. *leiolepis*) were planted. In the autumn of the next year, a predetermined amount of EC formulation containing pyridate as an active ingredient was diluted with water (in an amount corresponding to 2,000 L/ha) and applied for foliar treatment by a small sprayer.

On the 220th day after treatment, the state of growth of the green *kyllinga* was visually observed to determine the growth inhibition rate (%). The results are shown in Table 5.

TABLE 5

| Compound | Dose (g/ha) | Growth inhibition rate (%) of green *kyllinga* |
|---|---|---|
| Pyridate | 2000 | 100 |
|  | 4000 | 100 |

Test Example 6

Upland field soil was put into a 1/1,000,000 ha pot, and seeds of persian speedwell (*Veronica persica* Poir.) were sown. When the persian speedwell reached 4.3 to 5.2-leaf stage, predetermined amounts of EC formulation containing pyridate as an active ingredient and ONEHOPE NYUZAI (tradename) were diluted with water (in an amount corresponding to 300 L/ha) and applied for foliar treatment by a small sprayer.

On the 14th day after treatment, the state of growth of the persian speedwell was visually observed to determine the growth inhibition rate (%). The growth inhibition rate (%) (measured value) and the growth inhibition rate (%) calculated in the same manner as in the above Test Example 1 are shown in Table 6.

TABLE 6

| Compound | Dose (g/ha) | Growth inhibition rate (%) of persian speedwell Measured value | Growth inhibition rate (%) of persian speedwell Calculated value |
|---|---|---|---|
| Pyridate | 300 | 70 | — |
| Nicosulfuron | 100 | 5 | — |
| Pyridate + Nicosulfuron | 300 + 100 | 78 | 72 |

Test Example 7

Upland field soil was put into a 1/1,000,000 ha pot, and seeds of summer grass (*Digitaria ciliaris* (Retz.) Koeler) were sown. When the summer grass reached 4.0 to 5.0-leaf stage, predetermined amounts of EC formulation containing pyridate as an active ingredient and Monument WG (tradename) were diluted with water (in an amount corresponding to 300 L/ha) and applied for foliar treatment by a small sprayer.

On the 7th day after treatment, the state of growth of the summer grass was visually observed to determine the growth inhibition rate (%). The growth inhibition rate (%) (measured value) and the growth inhibition rate (%) calculated in the same manner as in the above Test Example 1 are shown in Table 7.

TABLE 7

| Compound | Dose (g/ha) | Growth inhibition rate (%) of summer grass Measured value | Growth inhibition rate (%) of summer grass Calculated value |
|---|---|---|---|
| Pyridate | 300 | 8 | — |
| Trifloxysulfuron Na salt | 100 | 40 | — |
| Pyridate + Trifloxysulfuron Na salt | 300 + 100 | 55 | 45 |

Test Example 8

Upland field soil was put into a 1/1,000,000 ha pot, and seeds of summer grass (*Digitaria ciliaris* (Retz.) Koeler) were sown. When the summer grass reached 4.0 to 5.0-leaf stage, predetermined amounts of EC formulation containing pyridate as an active ingredient and INPOOL DF (tradename) were diluted with water (in an amount corresponding to 300 L/ha) and applied for foliar treatment by a small sprayer.

On the 14th day after treatment, the state of growth of the summer grass was visually observed to determine the growth inhibition rate (%). The growth inhibition rate (%) (measured value) and the growth inhibition rate (%) calculated in the same manner as in the above Test Example 1 are shown in Table 8.

TABLE 8

| Compound | Dose (g/ha) | Growth inhibition rate (%) of summer grass Measured value | Growth inhibition rate (%) of summer grass Calculated value |
|---|---|---|---|
| Pyridate | 3000 | 50 | — |
| Halosulfuron-methyl | 150 | 0 | — |

TABLE 8-continued

| Compound | Dose (g/ha) | Growth inhibition rate (%) of summer grass | |
|---|---|---|---|
| | | Measured value | Calculated value |
| Pyridate + Halosulfuron-methyl | 3000 + 150 | 63 | 50 |

Test Example 9

Upland field soil is put into a 1/1,000,000 ha pot, and seeds of broadleaves or cyperaceae are sown. When the sown weeds reach 4 to 6-leaf stage, from 1,000 to 3,000 gai/ha of Lentagran WP (tradename) and from 20 to 40 gai/ha of SHIBAGEN DF (tradename) are diluted with water (in an amount corresponding to 300 L/ha) and applied for foliar treatment by a small sprayer.

On the 14 to 28th day after treatment, the state of growth of the weeds is visually observed to determine the growth inhibition rate (%) in the same manner as in the above Test Example 1. As a result, the composition of the present invention has the same remarkable growth inhibition rate and remarkable synergistic effect as in Test Example 1.

Test Example 10

Upland field soil was put into a 1/1,000,000 ha pot, and rhizomes of green *kyllinga* (*Kyllinga brevifolia* Rottb. var. *leiolepis*) were planted. When the green *kyllinga* reached a height of from 6 to 7 cm, predetermined amounts of Lentagran WP (tradename) and WG formulation containing as an active ingredient amicarbazone having the same mode of action as pyridate (tradename: Dinamic, manufactured by Arysta Life Science) were diluted with water (in an amount corresponding to 2,000 L/ha) and applied for foliar treatment by a small sprayer. Separately, upland field soil was put into a 1/300,000 ha pot, and turf of manilagrass (*Zoysia matrella* (L.) Merr.) was put. After the manilagrass took root, predetermined amounts of Lentagran WP (tradename) and Dinamic (tradename) were diluted with water (in an amount corresponding to 2,000 L/ha) and applied for foliar treatment by a small sprayer.

On the 27th day after treatment, the state of growth of green *kyllinga* was visually observed, and on the 28th day after treatment, the state of growth of the manilagrass was visually observed, to determine the growth inhibition rate (%). The results are shown in Table 9.

TABLE 9

| Compound | Dose (g/ha) | Growth inhibition rate (%) of green *kyllinga* | Growth inhibition rate (%) of manilagrass |
|---|---|---|---|
| Pyridate | 2000 | 76 | 5 |
| | 4000 | 94 | 15 |
| | 8000 | — | 15 |
| Amicarbazone | 400 | 30 | — |
| | 800 | 86 | 30 |

As evident from the results in Table 9, amicarbazone (the doses are practical doses) having the same mode of action as pyridate cannot simultaneously satisfy a sufficient growth inhibition rate of green *kyllinga* and safety for turfgrass. However, surprisingly, pyridate (doses are practical doses) has high activity against green *kyllinga* and has high safety for turfgrass, and was found to be capable of satisfying both sufficient growth inhibition rate of green *kyllinga* and safety for turfgrass simultaneously.

INDUSTRIAL APPLICABILITY

According to the present invention, a high active herbicidal composition having a broad herbicidal spectrum can be provided.

The entire disclosure of Japanese Patent Application No. 2012-052563 filed on Mar. 9, 2012 including specification, claims and summary is incorporated herein by reference in its entirety.

The invention claimed is:

1. A herbicidal composition comprising synergistically effective amounts of (A) pyridate or its salt and (B) at least one sulfonylurea compound selected from the group consisting of flazasulfuron and its salts; trifloxysulfuron and its salts; chlorimuron, its alkyl esters, and their salts; and halosulfuron, its alkyl esters, and their salts; wherein the weight ratio of (A) to (B) is from 200:1 to 0.75:1.

2. A method for controlling undesired plants or inhibiting growth, which comprises applying the herbicidal composition as defined in claim 1 in synergistically effective amounts to the undesired plants or to a place where they grow.

3. The method according to claim 2, wherein (B) of the herbicidal composition is flazasulfuron or its salts.

4. The method according to claim 3, wherein (A) is applied in an amount of from 200 to 5,000 g/ha and (B) is applied in an amount of from 10 to 150 g/ha.

5. The method according to claim 3, wherein the undesired plant is green *kyllinga*.

6. The method according to claim 3, wherein the undesired plant is green *kyllinga* having lowered sensitivity to herbicides.

7. The method according to claim 2, wherein (A) is applied in an amount of from 200 to 5,000 g/ha and (B) is applied in an amount of from 10 to 500 g/ha.

8. The method according to claim 2, wherein the undesired plant is green *kyllinga*.

9. The method according to claim 2, wherein the undesired plant is green *kyllinga* having lowered sensitivity to herbicides.

10. The herbicidal composition according to claim 1, wherein (B) is flazasulfuron or its salts.

11. The herbicidal composition according to claim 10, wherein the mixing ratio of (A) to (B) is from 200:1 to 1.3:1 by the weight ratio.

12. A method for controlling green *kyllinga* or inhibiting its growth, which comprises applying a herbicidally effective amount of (A) pyridate or its salt to the green *kyllinga* or to a place where it grows, wherein the green *kyllinga* is green *kyllinga* having lowered sensitivity to at least one sulfonylurea compound selected from the group consisting of flazasulfuron, trifloxysulfuron, chlorimuron and its alkyl ester, halosulfuron and its alkyl ester, and their salts, wherein (A) pyridate or its salt is applied in an amount of from 1,200 to 5,000 g/ha.

13. The method according to claim 12, wherein the sulfonylurea compound is flazasulfuron or its salts.

* * * * *